United States Patent [19]

Desai et al.

[11] Patent Number: 5,688,806

[45] Date of Patent: Nov. 18, 1997

[54] SPIROAZACYCLIC DERIVATIVES AS SUBSTANCE P ANTAGONISTS

[75] Inventors: Manoj C. Desai, Emeryville, Calif.; Lawrence A. Vincent, Moosup, Conn.

[73] Assignee: Pfizer Inc., New York, N.Y.

[21] Appl. No.: 513,798

[22] PCT Filed: Dec. 10, 1993

[86] PCT No.: PCT/US93/11793

§ 371 Date: Oct. 12, 1995

§ 102(e) Date: Oct. 12, 1995

[87] PCT Pub. No.: WO94/20500

PCT Pub. Date: Sep. 15, 1994

Related U.S. Application Data

[63] Continuation of Ser. No. 26,382, Mar. 4, 1993, abandoned.

[51] Int. Cl.[6] .................. A61K 31/445; C07D 471/10
[52] U.S. Cl. ............................... 514/278; 546/16
[58] Field of Search .................. 514/278; 540/1, 540/202, 356, 453, 488, 489, 524; 544/6, 70, 230; 546/15, 16

[56] References Cited

U.S. PATENT DOCUMENTS

| | | | |
|---|---|---|---|
| 4,804,665 | 2/1989 | Goto et al. | 514/278 |
| 4,940,795 | 7/1990 | Tsukamoto et al. | 546/16 |
| 5,075,317 | 12/1991 | Wu et al. | 514/278 |
| 5,162,339 | 11/1992 | Lowe, III | 514/305 |
| 5,373,003 | 12/1994 | Lowe, III | 514/216 |
| 5,393,762 | 2/1995 | Desai et al. | 514/331 |

OTHER PUBLICATIONS

Maggi, C.A. et al, J. Auton. Pharmacol. 1993, 13, pp. 23–93.

Primary Examiner—C. Warren Ivy
Assistant Examiner—Garth M. Dahlen
Attorney, Agent, or Firm—Peter C. Richardson; Paul H. Ginsburg; Karen DeBenedictis

[57] ABSTRACT

The present invention relates to novel spirocyclic piperidine derivatives and related compounds and, specifically, to compounds of the formula

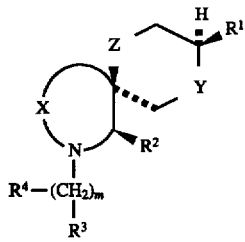

wherein X, Z, Y, $R^1$, $R^2$, $R^3$, $R^4$ and m are as defined in the specification, and to intermediates used in the synthesis of such compounds. The novel compounds of formula I are useful in the treatment of inflammatory and central nervous system disorders, as well as other disorders.

15 Claims, No Drawings

SPIROAZACYCLIC DERIVATIVES AS SUBSTANCE P ANTAGONISTS

This application is a 371 of PCT/US93/11793 filed Dec. 10, 1993 which is a Continuation of Ser. No. 08/026,382 filed Mar. 4, 1993, now abandoned.

BACKGROUND OF THE INVENTION

The present invention relates to novel spirocyclic piperidine derivatives and related compounds, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses a characteristic amino acid sequence that is illustrated by D. F. Veber et al. in U.S. Pat. No. 4,680,283.

The following references refer, collectively, to quinuclidine, piperidine, and azanorbornane derivatives and related compounds that exhibit activity as substance P receptor antagonists: U.S. Pat. No. 5,162,339, which issued on Nov. 11, 1992; U.S. patent application Ser. No. 724,268, filed Jul. 1, 1991; PCT Patent Application PCT/US 91/02853, filed Apr. 25, 1991; PCT Patent Application PCT/US 91/03369, filed May 14, 1991; PCT Patent Application PCT/US 91/05776, filed Aug. 20, 1991; PCT Patent Application PCT/US 92/00113, filed Jan. 17, 1992; PCT Patent Application PCT/US 92/03571, filed May 5, 1992; PCT Patent Application PCT/US 92/03317, filed Apr. 28, 1992; PCT Patent Application PCT/US 92/04697, filed Jun. 11, 1992; U.S. patent application Ser. No. 766,488, filed Sep. 26, 1991; U.S. patent application Ser. No. 790,934, filed Nov. 12, 1991; PCT Patent Application PCT/US 92/04002, filed May 19, 1992; Japanese Patent Application 065337/92, filed Mar. 23, 1992; U.S. patent application Ser. No. 932, 392, filed Aug. 19, 1992; and U.S. patent application Ser. No. 988,653, filed Dec. 10, 1992.

SUMMARY OF THE INVENTION

The present invention relates to compounds of the formula

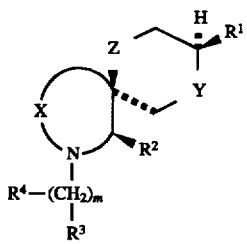

I wherein Z is NH, O or $CH_2$;

$R^1$ is phenyl optionally substituted with one or more substituents, preferably with from one to three substituents, independently selected from hydrogen, halo, nitro, ($C_1$–$C_{10}$) alkyl optionally substituted with from one to three fluorine atoms, ($C_1$–$C_{10}$)alkoxy optionally substituted with one to three fluorine atoms, trifluoromethyl, hydroxy, phenyl, cyano, amino, ($C_1$–$C_6$)-alkylamino, di-($C_1$–$C_6$)alkylamino,

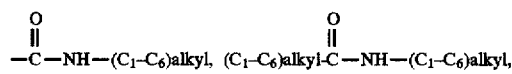

($C_1$–$C_4$)alkoxy($C_1$–$C_4$)alkyl, —S(O)$_v$— ($C_1$–$C_{10}$)-alkyl wherein v is zero, one or two, —S(O)$_v$-aryl wherein v is zero, one or two, —O-aryl, —SO$_2$NR$^9$R$^{10}$ wherein each of $R^4$ and $R^5$ is, independently, ($C_1$–$C_6$)alkyl, or $R^4$ and $R^5$, together with the nitrogen to which they are attached, form a saturated ring containing one nitrogen and from 3 to 6 carbons

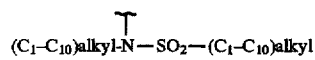

wherein one or both of the alkyl moieties may optionally be substituted with from one to three fluorine atoms, —N(SO$_2$-($C_1$–$C_{10}$)alkyl)$_2$ and

and wherein the aryl moieties of said —S(O)-aryl, —O-aryl and

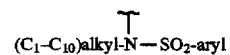

are independently selected from phenyl and benzyl and may optionally be substituted with from one to three substituents independently selected from ($C_1$–$C_4$)alkyl, ($C_1$–$C_4$)alkoxy and halo;

or $R^1$ is phenyl substituted with a group having the formula

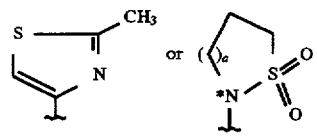

wherein a is 0, 1 or 2 and the asterisk represents a position meta to the point of attachment of $R^1$;

$R^2$ is selected from ($C_1$–$C_6$) straight or branched alkyl, ($C_3$–$C_7$)cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl ($C_2$–$C_6$)alkyl, benzhydryl and benzyl, wherein each of said aryl and heteroaryl groups and the phenyl moieties of said benzyl, phenyl ($C_2$–$C_6$)alkyl and benzhydryl may optionally be substituted with one or more substituents, preferably with from one to three substituents, independently selected from halo, nitro, ($C_1$–$C_{10}$)alkyl optionally substituted with from one to three fluorine atoms, ($C_1$–$C_{10}$)alkoxy optionally substituted with from one to three fluorine atoms, amino, hydroxy-($C_1$–$C_6$)alkyl, ($C_1$–$C_6$) alkoxy-($C_1$–$C_6$)alkyl, ($C_1$–$C_6$)-alkylamino,

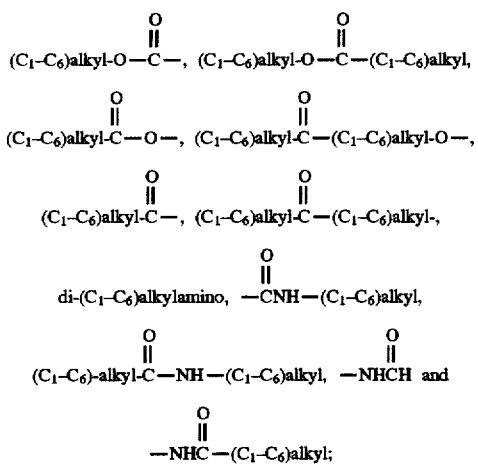

and wherein one of the phenyl moieties of said benzhydryl may optionally be replaced by naphthyl, thienyl, furyl or pyridyl;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^4$;

$R^3$ is selected from

$NHCH_2R^8$, $SO_2R^8$, $AR^5$, $CO_2H$ and the radicals set forth in the definitions of $R^2$, $R^6$ and $R^7$;

A is $CH_2$, nitrogen, oxygen, sulfur or carbonyl;

$R^8$ is $(C_1-C_6)$alkyl, hydrogen, phenyl or phenyl $(C_1-C_6)$alkyl;

$R^4$ is selected from oximino (=NOH) and the radicals set forth in the definitions of $R^2$, $R^6$ and $R^7$;

$R^5$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

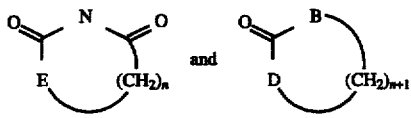

wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with $(C_1-C_6)$alkyl or $(C_2-C_6)$ spiroalkyl; and either any one pair of the carbon atoms of said $(CH_2)_n$ and $(CH_2)_{n+1}$ may be bridged by a one or two carbon atom linkage, or any one pair of adjacent carbon atoms of said $(CH_2)_n$ and $(CH_2)_{n+1}$ may form, together with from one to three carbon atoms that are not members of the carbonyl containing ring, a $(C_3-C_5)$ fused carbocyclic ring;

X is $(CH_2)_q$ wherein q is two or three and wherein one of the carbon-carbon single bonds in said $(CH_2)_q$ may option- ally be replaced by a carbon-carbon double bond, and wherein any one of the carbon atoms of said $(CH_2)_q$ may optionally be substituted with $R^6$, and wherein any one of the carbon atoms of said $(CH_2)_q$ may optionally be substituted with $R^7$;

$R^6$ and $R^7$ are independently selected from hydrogen, hydroxy, halo, amino, oxo (=O), cyano, hydroxy-$(C_1-C_6)$ alkyl, $(C_1-C_6)$alkoxy-$(C_1-C_6)$alkyl, $(C_1-C_6)$alkylamino,

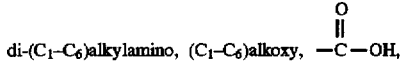

set forth in the definition of $R^2$; and

Y is $(CH_2)_z$ wherein z is zero or one;

with the proviso that: (a) when A is —$(CH_2)$— or carbonyl, $R^5$ cannot be furyl, pyridyl, isothiazolyl, oxazolyl, triazolyl, tetrazolyl, quinolyl, thiazolyl or thienyl; (b) when m is zero, one of $R^3$ and $R^4$ is absent and the other is hydrogen; (c) when $R^6$ or $R^7$ is attached to a carbon atom of X that is adjacent to the ring nitrogen, then $R^6$ or $R^7$, respectively, must be a substituent wherein the point of attachment is a carbon atom; and (d) when Z is O or $CH_2$, z is one.

Compounds identical to those of the formula I except that Z is O or $CH_2$ and z is zero are also expected to exhibit activity as substance P receptor antagonists.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylenebis-(2-hydroxy-3-naphthoate)]salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

Preferred of this invention include those compounds of the formula I wherein z is one.

Other preferred compounds of this invention are those compounds of the formula I wherein Z is NH.

Other preferred compounds of this invention are those compounds of the formula I wherein q is three.

Other preferred compounds of this invention are those compounds of the formula I wherein q is three, m is zero, R³ is hydrogen and R⁴ is absent.

Other preferred compounds of this invention are those compounds of the formula I wherein R¹ is phenyl substituted with from one to three substituents independently selected from (C₁-C₆)alkyl optionally substituted with from one to three fluorine atoms and (C₁-C₆)alkoxy optionally substituted with from one to three flourine atoms.

Other preferred compounds of this invention are those compounds of the formula I wherein z is one, m is zero, R⁴ is absent, and each of R³, R⁶ and R⁷ is hydrogen.

Specific preferred compounds of the formula I include the following:

(±)-[3R-[3α,6α(R*)]]-3-phenyl-7-phenyl-1,8-diazaspiro[5.5]undecane; and (±)-[3R-[3α,6α(R*)]]-3-(2-methoxyphenyl)-7-phenyl-1,8-diazaspiro[5.5]undecane.

Other compounds of the formula I include the following:

(±)-[3R-[3α,6α(R*)]]-3-(2-methoxy-5-trifluoromethoxyphenyl)-7-phenyl-1,8-diazaspiro[5.5]undecane;

(±)-[3R-[3α,6α(R*)]]-3-(5-chloro-2-methoxyphenyl)-7-phenyl-1,8-diazaspiro[5.5]undecane;

(±)-[3R-[3α,6α(R*)]]-3-(5-isopropyl-2-methoxyphenyl)-7-phenyl-1,8-diazaspiro[5.5]undecane;

(±)-[3R-[3α,6α(R*)]]-3-(5-tert.butyl-2-methoxyphenyl)-7-phenyl-1,8-diazaspiro[5.5]undecane;

(±)-[3R-[3α,6α(R*)]]-3-(2-methoxy-5-(N-methyl-N-methylsulfonylaminophenyl)-7-phenyl-1,8-diazaspiro[5.5]undecane;

(±)-[3R-[3α,6α(R*)]]-3-(2-iodophenyl)-7-phenyl-1,8-diazaspiro[5.5]undecane;

(±)-[3R-[3α,6α(R*)]]-3-(2-methoxy-4-methylphenyl)-7-phenyl-1,8-diazaspiro[5.5]undecane;

(±)-[3R-[3α,6α(R*)]]-3-(2-isopropoxyphenyl)-7-phenyl-1,8-diazaspiro[5.5]undecane;

(±)-[3R-[3α,6α(R*)]]-3-(2-difluoromethoxy-5-trifluoromethoxyphenyl)-7-phenyl-1,8-diazaspiro[5.5]undecane;

(±)-[3R-[3α,5α(R*)]]-3-(2-methoxyphenyl)-6-phenyl-1,7-diazaspiro[4.5]decane;

(±)-[3R-[3α,5α(R*)]]-3-(2-methoxy-5-trifluoromethoxyphenyl)-6-phenyl-1,7-diazaspiro[4.5]decane;

(±)-[3R-[3α,5α(R*)]]-3-(5-chloro-2-methoxyphenyl)-6-phenyl-1,7-diazaspiro[4.5]decane;

(±)-[3R-[3α,5α(R*)]]-3-(5-isopropyl-2-methoxyphenyl)-6-phenyl-1,7-diazaspiro[4.5]decane; and (±)-[3R-[3α,5α(R*)]]-3-(5-tert.butyl-2-methoxyphenyl)-6-phenyl-1,7-diazaspiro[4.5]decane.

Preferred compounds of this invention also include the pharmaceutically acceptable salts of the foregoing preferred compounds.

This invention also relates to compounds of the formulae

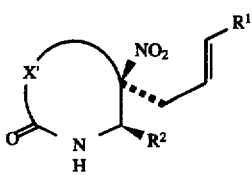

IV

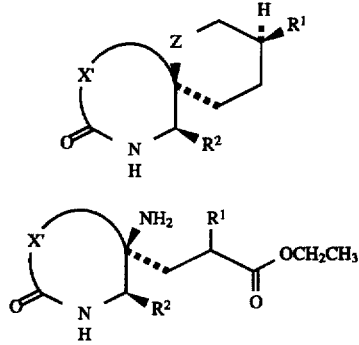

XVIII

XI

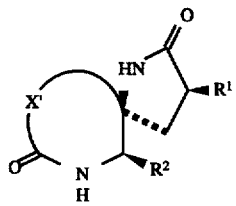

and

XII wherein Z, R¹ and R² are defined as above and X' is CH₂ or (CH₂)₂, and wherein the carbon-carbon single bond of (CH₂)₂ may optionally be replaced by a carbon-carbon double bond, and wherein any one of the carbon atoms of said CH₂ or (CH₂)₂ may optionally be substituted with R⁶, wherein R⁶ is defined as above, and wherein any one of the carbon atoms of said CH₂ or (CH₂)₂ may optionally be substituted with R⁷, wherein R⁷ is defined as above. These compounds are useful as intermediates in the synthesis of compounds of the formula I.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, gastrointestinal disorders such as emesis and colitis, psychosis, pain, urinary incontinence, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, gastrointestinal disorders such as emesis and colitis, psychosis, pain, urinary incontinence, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, gastrointestinal disorders such as emesis and colitis, psychosis, pain, urinary incontinence, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, gastrointestinal disorders such as emesis and colitis, psychosis, pain, urinary incontinence, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The compounds of the formula I may be prepared as described in the following reaction schemes and discussion. Unless otherwise indicated, $R^1$, $R^2$, $R^3$, $R^4$, X, X', Z, m and Y, and structural formulae I, IV, and VIII in the reaction schemes and discussion that follow are defined as above.

Scheme 1
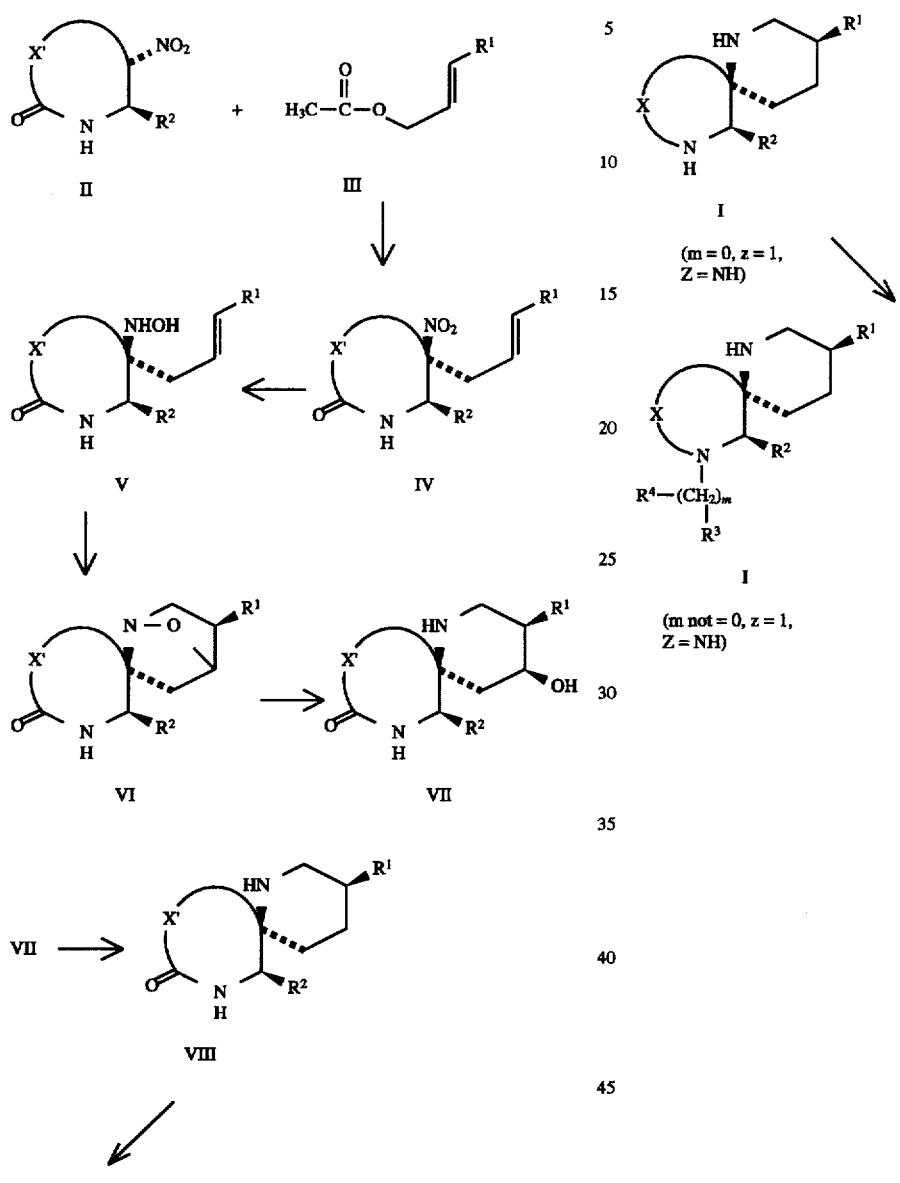
Scheme 2
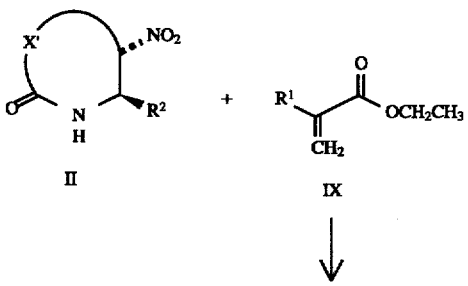

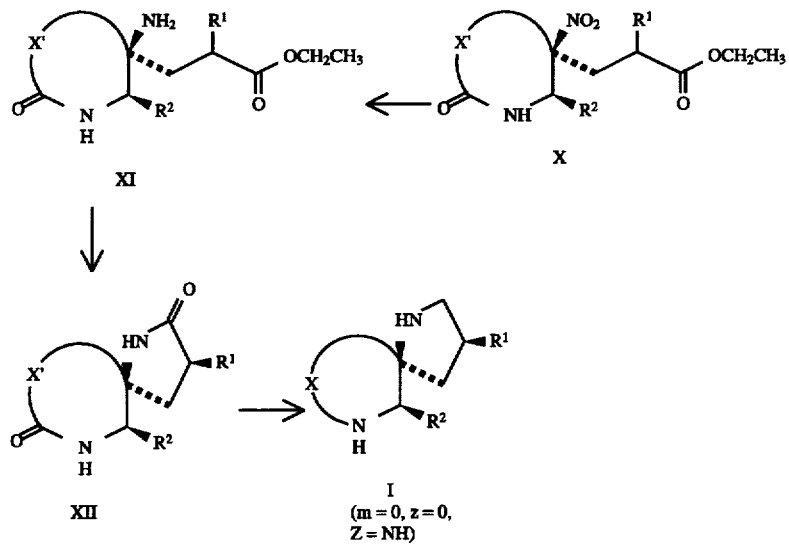

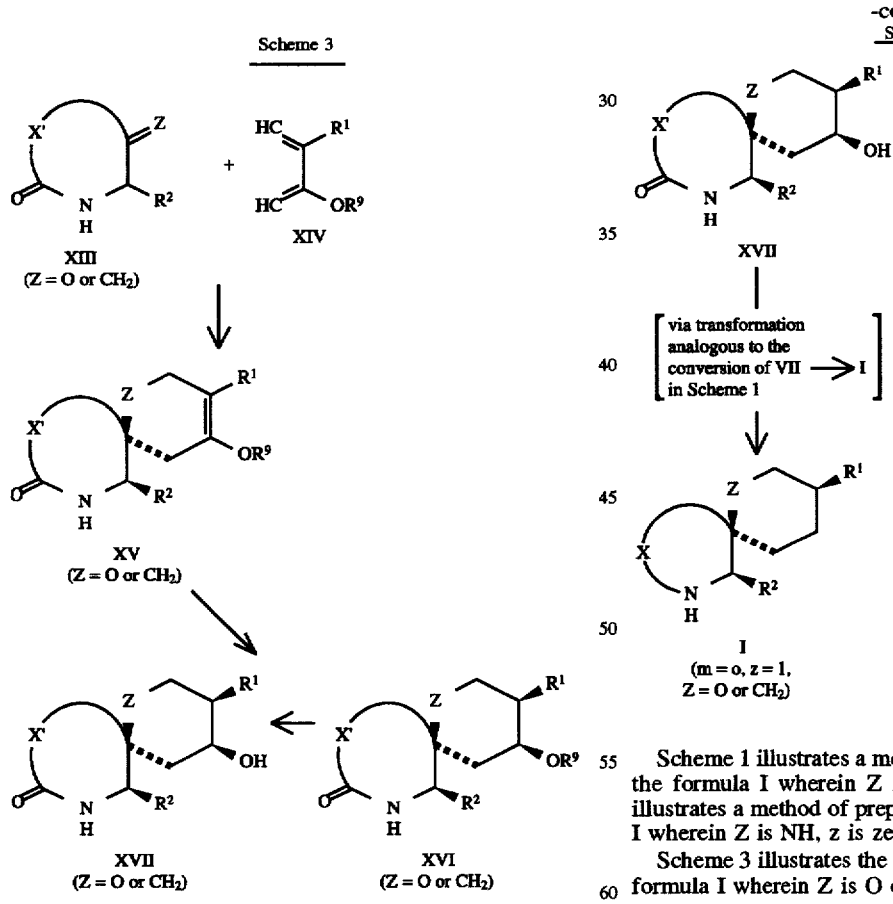

Scheme 1 illustrates a method of preparing compounds of the formula I wherein Z is NH and z is one. Scheme 2 illustrates a method of preparing compounds of the formula I wherein Z is NH, z is zero and m is zero.

Scheme 3 illustrates the preparation of compounds of the formula I wherein Z is O or $CH_2$, z is one and m is zero.

Referring to scheme 1, a compound of the formula II is reacted with a compound of the formula III in the presence of an alkali metal alkoxide (e.g., lithium methoxide, sodium methoxide, potassium t-butoxide or sodium t-butoxide) and tetrakis (triphenylphosphine) palladium to form a compound of the formula IV. This reaction is generally conducted in two steps. First, the alkali metal alkoxide is added to a lower alkanol solvent (e.g., ethanol or propanol) at a temperature from about 0° C. to about room temperature, for about 10–15 minutes, after which the mixture is evaporated to dryness. A water/tetrahydrofuran or water/glyme mixture is then added to the resulting solid. The compound of formula III and tetrakis (triphenylphosphine) palladium are then added to the resulting mixture. Preferably, triphenylphosphine is also added. This reaction is typically conducted at a temperature from about 0° C. to about 65° C., preferably about room temperature.

The compound of formula IV formed in the above step is then converted to the corresponding compound of formula V by reduction of the nitro group. This is accomplished by reacting the compound of formula IV with a suitable ammonium salt (e.g., ammonium chloride, ammonium acetate or ammonium formate) and zinc. The preferred ammonium salt is ammonium acetate. The reaction is generally carried out in water, a lower alkanol or acetic acid, or a mixture of two or more of the foregoing, preferably in methanol or ethanol, at a temperature from about room temperature to about 100° C., preferably from about 60° C. to about 65° C.

Alternatively, the reduction may be carried at using aluminum amalgum as the reducing agent. Sovents that can be used with aluminum amalgum include THF, water and dioxane. The reaction temperature may range from about 0° C. to about 100° C. and is preferably about room temperature.

Reaction of the compound of formula V so formed with 37% aqueous formaldehyde or another form of formaldehyde (e.g., paraformaldehyde or S-trioxane) yields the corresponding compound of formula VI. Appropriate solvents for this reaction include toluene, benzene and xylenes. The preferred solvent is toluene. Appropriate temperatures range from about 100° C. to about 200° C., with about 120° C. being preferred.

The compound of formula VI may be converted into the corresponding compound of formula VII by the process described above for preparing compounds of the formula V from the corresponding compounds of formula IV. The preferred solvent, however, is water/acetic acid and the preferred ammonium salt is ammonium acetate.

A two step process is then used to prepare the corresponding compound of the formula VIII. In the first step, the compound of formula VII is reacted with 1,1'-thiocarbonyldiimidazole and an organic tertiary amine base, preferably triethylamine. Suitable solvents for this reaction include tetrahydrofuran (THF), dioxane and chlorinated hydrocarbons such as methylene chloride, chloroform and 1,2-dichloroethane. 1,2-Dichloroethane is preferred. Suitable temperatures range from about 50° C. to about 200° C., with about 75° C. being preferred. When the reaction is complete, the reaction mixture is then evaporated to dryness.

In the second step, the solid product from the above reaction is dissolved in a high boiling solvent at a temperature from about 100° C. to about 200° C., preferably about 120° C. Examples of solvents that may be used are toluene, xylenes, benzene, and THF. Toluene is preferred. Then, azobisisobutyronitrile (AIBN) is added to the reaction mixture, followed by tributyltin hydride, to produce the desired compound of formula VIII.

Compounds of the formula I wherein m is zero and z is one may then be prepared by reducing the corresponding compounds of the formula VIII. Examples of suitable reducing agents are lithium aluminum-hydride, borane dimethlysulfide in THF, borane in THF and sodium borohydride-titanium (IV) chloride. Best results are obtained using borane dimethylsulfide in THF. The reaction may be carried out at temperatures from about room temperature to about 150° C., and is preferably carried out at the reflux temperature of the solvent.

Compounds of the formula I wherein z is one and m is other than zero may be formed from the corresponding compounds wherein m is zero by reacting then with a compound of the formula $R^3-(CH_2)_m-X"$, wherein X" is halo, and wherein any one of the carbon-carbon single bonds of said $(CH_2)_m$, wherein both carbon atoms of such bond are bonded to each other and to another carbon atom in the $(CH_2)_m$ chain, may optionally be replaced by a carbon-carbon double bond or carbon-carbon triple bond, and wherein one of the carbons of said $(CH_2)_m$ may optionally be substituted with $R^4$. This reaction is typically carried out in the presence of a base such as triethylamine or potassium t-butoxide, in a polar solvent such as methylene chloride or dichloroethane, and at a temperature from about room temperature to about 150° C. Preferably, the reaction is carried out at the reflux temperature in methylene chloride in the presence of triethylamine.

As indicated above, compounds of the formula I wherein z is zero and m is zero may be prepared as described in reaction scheme 2 above. Referring to scheme 2, a compound of the formula II is reacted with a compound of the formula IX and either tetramethyl quanidine, diazabicycloundecane or an alkali metal alkoxide (e.g., sodium methoxide or potassium methoxide) to form a compound of the formula X. This reaction is generally carried out in a lower alkanol solvent such as methanol or ethanol or an ethereal solvent such as THF, dioxane or ethyl ether at a temperature from about 0° C. to about 100° C. It is preferably carried out in THF at about room temperature.

Reduction of the nitro substituted compound of formula X yields the corresponding amine of formula IX. Suitable reducing agents include Raney nickel/hydrogen, 10% palladium on charcoal/hydrogen, and aluminum amalgam. Preferably, the reduction is carried out using Raney nickel in ethanol under a hydrogen gas pressure of about 3 atm and at a temperature of about 25° C. Temperatures from about 10° C. to about 60° C. and pressures from about 1 to about 10 atmospheres are also suitable.

The compound of formula XI produced in the above step may be converted into the corresponding compound of formula XII by heating it in the presence or absence of a solvent at a temperature from about 80° C. to about 150° C., preferably at the reflux temperature of the solvent. Suitable solvents include toluene, zylenes and nitrobenzene. This reaction produces both the compound of formula XII and its enantiomer. The desired isomer can be isolated using column chromatography.

Reduction of the compound of formula XII yields the corresponding compound of the formula I wherein z is zero and m is zero. Suitable reducing agents include borane dimethylsulfide in THF, lithium aluminum hydride, borane in THF and sodium borohydride-titanium (IV) chloride. Best results are obtained by using borane dimethylsulfide in THF. This reaction may be carried out at temperatures from about room temperature to about 150° C., and is preferably carried out at the reflux temperature of the solvent.

As indicated above, scheme 3 illustrates the preparation of compounds of the formula I wherein Z is O or $CH_2$, z is one and m is zero. Referring to scheme 3, a compound of the formula XIII is reacted with a compound of the formula XIV wherein $R^9$ is trimethylsilyl or tert-butyldimethylsilyl to form a compound of the formula XV. When Z is oxygen, the reaction is carried out in the presence of a Lewis acid, preferably boron trifluoride etherate. Other Lewis acids that may be used are diethyl aluminium chloride, aluminium trichloride, titanium tetrachloride are zinc dibromide. The reaction, when conducted in the response of a Lewis acid, may be carried out in any of a variety of reaction inert solvents such as THF, methylene chloride or chloroform. Suitable reaction temperatures range from about –78° C. to about 0° C. About 0° C. is preferred.

When Z is $CH_2$, the reaction of compounds of the formulae XIII and XIV is generally carried in a reaction inert solvent such as benzene or xylenes, by heating the reaction mixture to a temperature from about 120° C. to about 200° C., preferably to about 200° C.

Hydrogenation of resulting compound of the formula XV by methods well known to those skilled in the art yields the corresponding compound of formula XVI. The hydrogenation may be accomplished by treating the compound of formula XV with hydrogen gas in the presence of a metal catalyst such as palladium on charcoal, platinum on charcoal or platinum dioxide, preferably palladium on charcoal, and in the presence of an acid such as trifluoroacetic acid or hydrochloric acid. A polar inert solvent is generally used. The preferred solvent is ethanol. This reaction is typically carried out at a pressure of about 1.5 atm to about 5 atm, preferably at about 3.0 atm, at a temperature from about 0° C.–60° C., preferably at about 25° C.

The compound of formula XVI formed in the above step may be converted into the corresponding compound of formula XVII by reacting it with a fluoride anion (e.g., hydrogen fluoride in acetonitrile or tetrabutylammonium fluoride in THF). This reaction may be carried out at a temperature from about 15° C. to about 100° C. It is preferably carried out at about room temperature.

Compounds of the formula XVII, prepared as described above, may be converted into the corresponding compounds of the formula I wherein m is zero and z is one by the procedure depicted in scheme 1 and described above for converting compounds of the formula VII into compounds of the formula I.

Compounds of the formula I that were prepared by the procedure of scheme 2 or scheme 3 and wherein m is zero may be converted into the corresponding compounds of the formula I wherein and m is other than zero by the method depicted in scheme 1 and described above for forming compounds of the formula I wherein z is one and m is other than zero.

The preparation of other compounds of the formula I not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and their pharmaceutically acceptable salts (hereinafter referred to as "the therapeutic compounds of this invention") are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The therapeutic compounds of this invention exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, gastrointestinal disorders such as emesis and colitis, psychosis, pain, urinary incontinence, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The therapeutic compounds of this invention can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of this invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of this invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the therapeutic compounds of this invention topically when treating inflammatory conditions of the skin and this may preferably be done by way of creams, jellies, gels, pastes, ointments and the like, in accordance with standard pharmaceutical practice.

The activity of the therapeutic compounds of this invention as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma Extravasation in the Skin

Plasma extravasation is induced by intradermal administration of substance P (50 µl, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced Plasma Extravasation

Plasma extravasation is induced by intraperitoneal injection of capsaicin (10 ml of 30 µM solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

19 c. Acetic Acid-induced Abdominal Stretching

Male ddY mice (SLC, Japan), weighing 14–18 g. were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance P-induced Hyperlocomotor Paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(±)-[3R-[3α,4α,6α(R*)]]-3-(2-methoxyphenyl)-7-phenyl-1,8-diazaspiro[5.5]undecane A. (±) -[5S-[5α,5(E)],6α]]-5-[3-(2-methoxyphenyl)-2-propenyl]-5-nitro-6-phenyl-2-piperidinone Litium methoxide (3.0 gm, 78 mmole) was added to a stirred suspension of (±)-trans-5-nitro-2-oxo-6-phenylpiperidine in methanol (50 mL) at 0° C. After 10 minutes, the volatiles were stripped off under vacuum. To the resulting while solid, THF (500 mL), water (40 mL), triphenylphosphine (1.0 gm, 3.9 mmole), 2-methoxy cinnamyl acetate (16.2 gm, 78 mmole), and tetrakis (triphenylphosphine)palladium(0) (4.5 gm, 3.9 mmole) were added. The mixture was stirred at ambient temperature for 18 hours, and the volatiles were removed under vacuum. The resulting solids were dissolved in ethyl acetate and washed with 1N hydrochloric acid (1×200 mL), water (1×200 mL), and brine (1×100 mL). The organic layer was dried and concentrated to afford a semisolid, which was triturated with ether-ethanol to yield (±)-[5S-[5α,5(E),6α]]-5-[3-(2-methoxyphenyl)-2-propenyl]-5-nitro-6-phenyl-2-piperidinone (24 gm, 84%).

M.p. 180°–183° C.

$^1$H NMR (500 MHz, CDCl$_3$) δ 2.21 (m, 1H), 2.5–2.64 (m, 2H), 2.82 (dd, J=4, 15 Hz 1H), 3.07 (dd, J=9, 16 Hz 1H), 3.4 (dd, J=6, 15 Hz 1H), 3.85 (s, 3H), 4.91 (bd, J=2 Hz, 1H), 5.95 (ddd, J=6, 9, 15 Hz 1H), 6.33 (bd, J=2 Hz 1H), 6.7–7.0 (m, 2H), 7.15–7.4 (m, 8H).

$^{13}$C NMR (CDCl$_3$) δ 170.36, 156.59, 135.64, 131.18, 129.38, 129.21, 128.83, 127.87, 126.81, 125.01, 120.59, 120.49, 110.82, 90.31, 62.9, 55.4, 39.81, 27.78, 21.94.

B. (±)-[5S-[5α,5(E),6α]]-5-(hydroxyamino)-5-[3-(2-methoxyphenyl)-2-propenyl]-6-phenyl-2-piperidinone To a stirred solution of (±)-[5S-[5α,5(E),6α]]-5-[3-(2-methoxyphenyl)-2-propenyl]-5-nitro-6-phenyl-2-piperidinone (9.15 gm, 25 mmole) and ammonium acetate (9.62 gm, 125 mmole) in methanol (400 mL) on a steam bath (internal temperature 60°–65° C.), zinc dust (4.1 gm, 62.5 mmole) was added slowly with swirling over a period of 15 minutes. After 20 more minutes, the reaction mixture was cooled, filtered through Celite® and concentrated under vacuum to an oil, which was dissolved in ethyl acetate. The organic layer was washed with 1N sodium hydroxide (NaOH) (2×200 mL), water, brine and dried anhydrous magnesium sulfate (MgSO$_4$). The organic layer was concentrated to afford a brown oil, which was triturated with ether to yield (±)-[5S-[5α,5(E),6α]]-5-(hydroxyamino)-5-[3-(2-methoxyphenyl) -2-propenyl]-6-phenyl-2-piperidinone (6.0 gm, 68%).

M.p. 187°–189° C.

$^1$H NMR (500 MHz, CDCl$_3$) δ 1.59 (dd, J=7, 14HZ, 1H), 1.77 (dd, J=7, 14 HZ, 1H), 2.4–2.7 (m, 3H), 2.89 (dd, J=7, 14 Hz, 1H), 3.86 (s, 3H), 4.57 (s, 1H), 5.48 (bs, 1H), 6.24 (quin, J=7 Hz 1H), 6.37 (bs, 1H), 6.7–7.0 (m, 2H), 7.2–7.5 (m, 9H).

$^{13}$C NMR (CDCl$_3$) δ 172.31, 156.38, 137.55, 128.69, 128.57, 128.45, 128.32, 126.52, 126.19, 120.57, 125.1, 110.78, 62.24, 59.62, 55.42, 37.02, 27.52, 23.71.

C. (±)-[1S-[1α,2α(S*),4α, 5α]]-5-(2-methoxyphenyl)-2'-phenyl-spiro[7-oxa-1-azabicyclo[2.2.1]heptane-2,3'-piperidin]-6'-one A mixture of (±) -[5S-[5α,5(E),6α]]-5-(hydroxyamino)-5-[3-(2-methoxyphenyl)-2-propenyl]-6-phenyl-2-piperidinone (0.176 gm, 0.5 mmole), 37% formaldehyde (0.05 mL, 0.6 mmole) and toluene (6 mL) was maintained at 120° C. for 3 hours. The reaction mixture was cooled, concentrated under vacuum, and triturated with ether-hexane to afford (±)-[1S-[1α,2α(S*), 4α,5α]]-5-(2-methoxyphenyl)-2'-phenyl-spiro[7-oxa-1-azabicyclo[2.2.1] heptane-2,3'-piperidin]-6'-one as a white solid (0.11 gm, 60%).

M.p. 284°–286° C.

$^1$H NMR (500 MHz, CDCl$_3$) δ 1.65–1.7 (m, 1H), 1.73 (d, J=12 Hz 1H), 2.0–2.1 (m, 1H), 2.31 (dd, J=5, 12 Hz 1H), 2.63 (ddd, J=8, 11, 19 Hz 1H), 2.78 (ddd, J=2, 7, 19 Hz 1H), 2.86 (dd, J=5, 13 Hz 1H), 3.46 (dd, J=5.5, 8 Hz 1H), 3.53 (dd, J=8, 12.5 Hz 1H), 3.81 (s, 3H), 4.57 (d, J=3 Hz 1H), 4.87 (d, J=5 Hz 1H), 6.07 (bs, 1H), 6.83 (d, J=8 Hz 1H), 6.94 (t, J=7.5 Hz 1H), 7.1–7.5 (m, 7H).

$^{13}$C NMR (CDCl$_3$) δ 171.69, 156.24, 139.52, 129.18, 128.96, 127.74, 127.69, 127.49, 126.74, 120.98, 109.9, 86.42, 69.33, 64.4, 58.61, 55.29, 44.89, 43.22, 29.13, 23.38.

D. (±)-[3R-[3α,4α,6α(R*)]]-4-hydroxy-3-(2-methoxyphenyl)-7-phenyl-1,8-diazaspiro[5.5]undecan-9-one To a stirred suspension of (±)-[1S-[1α,2α(S*), 4α,5α]]-5-(2-methoxyphenyl)-2'-phenyl-spiro[7-oxa-1-azabicyclo [2.2.1]heptane-2,3'-piperidin]-6,-one (4.25 gm, 11.6 mmole) in acetic acid (100 mL) and water (20 mL) at 70° C., zinc dust (2.5 gm, 38.6 mmole) was added slowly with stirring over a period of 15 minutes. After one hour, the reaction mixture was cooled and added to a Erlenmeyer flask containing 25% aq. NaOH (300mL) and ethyl acetate (500 mL). The content of the flask was filtered through Celite® and the aqueous phase was extracted with additional ethyl acetate. The combined ethyl acetate layer was washed with water, brine and dried (anhyd. MgSO$_4$). The organic layer was concentrated to yield (±)-[3R-[3α,4α,6α(R*)]]-4-hydroxy-3-(2-methoxyphenyl)-7-phenyl-1,8-diazaspiro[5.5] undecan-9-one (4.15 gm, 99%).

M.p. 150°–152° C.

$^1$H NMR (500 MHz, CDCl$_3$) δ 1.57 (bs, 1H), 1.72 (d, J=12 Hz 1H), 2–2.15 (m, 2H), 2.2–2.3 (m, 1H), 2.5–2.7 (m, 2H), 3.5–3.65 (m, 2H), 3.82 (s, 3H), 4.31 (bs, 1H), 5.24 (bs, 1H), 6.03 (bs, 1H), 6.8, (t, J=7.5 Hz 1H), 6.86 (dd, J=1, 8 Hz 1H), 7.1–7.5 (m, 7H).

$^{13}$C NMR (CDCl$_3$) δ 171.49, 157.1, 128.46, 128.29, 128.41, 127.79, 120.55, 110.31, 67.52, 62.47, 55.38, 40.72, 38.65, 36.49, 29.24, 28.08.

E. (±)-[3R-[3α,4α,6α(R*)]]-3-(2-methoxyphenyl)-7-phenyl-1,8-diazaspiro[5.5]undecan-9-one A mixture of (±)-[3R-[3α,4α,6α(R*)]]-4-hydroxy-3-(2-methoxyphenyl)-7-phenyl-1,8-diazaspiro[5.5]undecan-9-one (0.2 gm, 0.55mmole), 1,1'-thiocarbonyldiimidazole (0.194 gm, 1.1 mmole), triethylamine (0.111 gm, 1.1 mmole) and 1,2-dichloroethane was heated to 75° C. for 18 hours. The reaction mixture was dissolved in chloroform, washed (water and brine), dried (anhyd. MgSO$_4$) and concentrated to a yellow solid (370 mg). The yellow solid was dissolved in toluene (50 mL) at 120° C. and to it azobisisobutyronitrile (AIBN) (25 mgs) was added. Next, tributyltin hydride (0.32 gm, 1.1 mmole) in toluene (5 mL) was added over a period of 0.5 hour. After an additional 0.5 hour, the reaction mixture was concentrated, and the residue was triturated with hexane-ether to afford pure (±)-[3R-[3α,4α,6α(R*)]]-3-(2-methoxyphenyl)-7-phenyl-1,8-diazaspiro[5.5]undecan-9-one (0.077, 40%).

M.p. 152°–155° C.

$^1$H NMR (500 MHz, CDCl$_3$) δ 1.5–1.58 (m, 1H), 1.6–1.7 (m, 1H), 1.9–2.05 (m, 2H), 2.3–2.4 (m, 2H), 2.57–2.7 (m, 2H), 2.9–3.0 (m, 1H), 3.15–3.25 (m, 1H), 3.83 (s, 3H), 4.91 (d, J=3 Hz 1H), 6.06 (bs, 1H), 6.7–7.4 (m, 9H).

$^{13}$C NMR (CDCl$_3$) δ 171.72, 157.16, 138.90, 132.04, 128.99, 128.45, 128.33, 128.2, 127.91, 127.31, 126.94, 125.26, 120.4, 110.34, 59.33, 55.19, 51.64, 47.13, 35.95, 32.03, 30.48, 28.37, 25.61.

F. (±)-[3R-[3α,6α(R*)]]-3-(2-methoxyphenyl)-7-phenyl-1,8-diazaspiro[5.5]undecane Borane dimethylsulfide in tetrahydrofuran (THF) (2M, 0.3 mL, 0.3 mmole) was added to a solution of (±)-[3R-[3α,4α,6α(R*)]]-3-(2-methoxyphenyl)-7-phenyl-1,8-diazaspiro[5.5]undecan-9-one (0.035 gm, 0.1 mmole) in tetrahydrofuran (2 mL) under nitrogen, and the reaction mixture was refluxed for 18 hours. At the end of this period, the reaction mixture was cooled and the excess of the boran dimethylsulfide was cautiously decomposed by dropwise addition of methanol. The contents of the reaction mixture were then concentrated under vacuum. Ethanol (2 mL) and powdered potassium carbonate (10 mg) were added to the residue and the reaction mixture was refluxed (18 hours). Thereafter, the reaction mixture was concentrated under vacuum and the residue was extracted with methylene chloride (3×20 mL) and dried (anhydrous MgSO$_4$). The organic solvents were removed under vacuum to afford a residue which was chromatographed. Elution with 10% methanol in methylene chloride containing 1% ammonium hydroxide to give (±)-[3R-[3α,6α(R*)]]-3-(2-methoxyphenyl)-7-phenyl-1,8-diazaspiro[5.5]undecane as an oil. It was treated with excess hydrochloric acid-ether to afford a dihydrochloride salt which was crystallized from isopropyl alcohol to afford (+)-[3R-[3α,6α(R*)]]-3-(2-methoxyphenyl)-7-phenyl-1,8-diazaspiro[5.5]undecane dihydrochloride salt (34 mgs, 83%). The structure was further confirmed by X-ray crystallographic data.

M.p. 296°–298° C.

$^1$H NMR (500 MHz, CDCl$_3$) δ 1.15–1.35 (m, 3H), 1.55–1.63 (m, 2H), 1.7–1.85 (m, 2H), 2.34 (bd, J=12.4 Hz, 1H), 2.77 (dt, J=3, 12 Hz 1H), 2.87 (dd, J=4, 12 Hz 1H), 3.03–3.22 (m, 3H), 3.51 (s, 1H), 3.73 (s, 3H), 6.52 (dt, J=1, 7 Hz 1H), 6.71 (dd, J=1, 8 Hz, 1H), 7.02 (dt, J=2, 7 Hz 1H), 7.21 (dd, J=2, 7 Hz 1H), 7.24–7.35 (m, 4H), 7.45 (m, J=2, 8 Hz 1H).

$^{13}$C NMR (CDCl$_3$) δ 156.38, 141.84, 133.91, 129.46, 129.01, 127.39, 127.11, 126.17, 119.84, 109.52, 71.82, 55.10, 52.10, 47.78, 45.24, 33.80, 31.85, 31.42, 24.92, 21.94.

EXAMPLE 2

(+)-[3R-[3α,6α(R*)]]-3-phenyl-7-phenyl-1,8-diazaspiro [5.5]undecane $^1$H NMR (500 MHz, CDCl$_3$) δ 1.08 (m, 1H), 1.28 (m, 2H), 1.58 (m, 1H), 1.7 (m, 3H), 2.0 (m, 1H), 2.15 (m, 1H), 2.58 (d, J=12 Hz, 1H), 2.88 (m, 2H), 2.98 (m, 1H), 3.24 (dd, J=2, 11 Hz, 1H), 3.38 (bd, 1H), 3.65 (s, 1H), 6.75 (m, 2H), 7.1 (m, 3H), 7.38 (m, 3H), 7.58 (bs, 2H). The structure was confirmed by X-ray crystallography.

We claim:

1. A compound of the formula

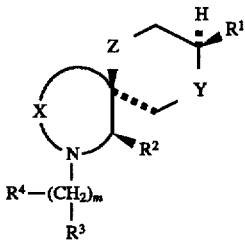

wherein Z is NH, O or CH$_2$;

R$^1$ is phenyl optionally substituted with one or more substituents, independently selected from hydrogen, halo, nitro, (C$_1$–C$_{10}$)alkyl optionally substituted with from one to three fluorine atoms, (C$_1$–C$_{10}$)alkoxy optionally substituted with from one to three fluorine atoms, trifluoromethyl, hydroxy, phenyl, cyano, amino, (C$_1$–C$_6$)-alkylamino, di-(C$_1$–C$_6$)alkylamino,

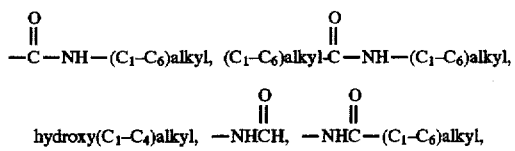

(C$_1$–C$_4$)alkoxy(C$_1$–C$_4$)alkyl, —S(O)$_v$-(C$_1$–C$_{10}$)-alkyl wherein v is zero, one or two, —S(O)$_v$-aryl wherein v is zero, one or two, —O-aryl, —SO$_2$R$^4$R$^5$ wherein each of R$^9$ and R$^{10}$ is, independently, (C$_1$–C$_6$)alkyl, or R$^9$ and R$^{10}$, together with the nitrogen to which they are attached, form a saturated ring containing one nitrogen and from 3 to 6 carbons,

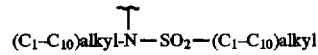

wherein one or both of the alkyl moieties may optionally be substituted with from one to three fluorine atoms, —N(SO$_2$-(C$_1$–C$_{10}$)alkyl)$_2$ and

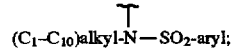

and wherein the aryl moieties of said —S(O)$_v$-aryl, —O-aryl and

are independently selected from phenyl and benzyl and may optionally be substituted with from one to three substituents independently selected from (C$_1$–C$_4$)alkyl, (C$_1$–C$_4$)alkoxy and halo;

or $R^1$ is phenyl substituted with a group having the formula

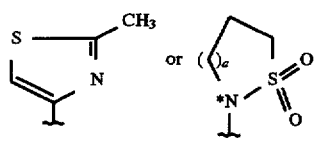

wherein a is 0, 1 or 2 and the asterisk represents a position meta to the point of attachment of $R^1$;

$R^2$ is selected from ($C_1$–$C_6$) straight or branched alkyl, ($C_3$–$C_7$) cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl ($C_2$–$C_6$)alkyl, benzhydryl and benzyl, wherein each of said aryl and heteroaryl groups and the phenyl moieties of said benzyl, phenyl ($C_2$–$C_6$)alkyl and benzhydryl may optionally be substituted with one or more substituents, independently selected from halo, nitro, ($C_1$–$C_{10}$)alkyl optionally substituted with from one to three fluorine atoms, ($C_1$–$C_{10}$)alkoxy optionally substituted with from one to three fluorine atoms, amino, hydroxy-($C_1$–$C_6$)alkyl, ($C_1$–$C_6$)alkoxy-($C_1$–$C_6$)alkyl, ($C_1$–$C_6$)-alkylamino,

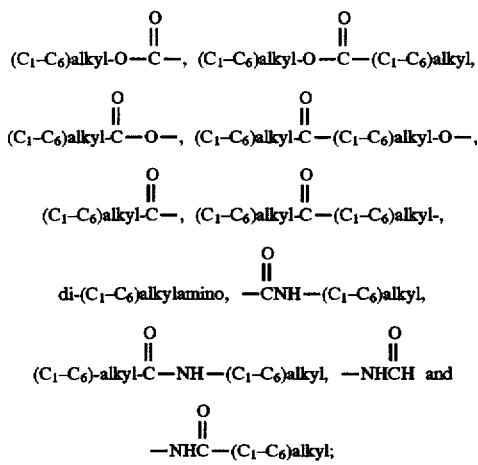

and wherein one of the phenyl moieties of said benzhydryl may optionally be replaced by naphthyl, thienyl, furyl or pyridyl;

m is an integer from 0 to 8 and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^4$;

$R^3$ is selected from

$NHCH_2R^8$, $SO_2R^8$, $AR^5$, $CO_2H$ and the radicals set forth in the definitions of $R^2$, $R^6$ and $R^7$;

A is $CH_2$, nitrogen, oxygen, sulfur or carbonyl;

$R^8$ is ($C_1$–$C_6$)alkyl, hydrogen, phenyl or phenyl ($C_1$–$C_6$) alkyl;

$R^4$ is selected from oximino (=NOH) and the radicals set forth in the definitions of $R^2$, $R^6$ and $R^7$;

$R^5$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

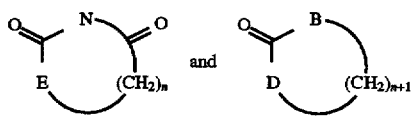

wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with ($C_1$–$C_6$)alkyl or ($C_2$–$C_6$) spiroalkyl; and either any one pair of the carbon atoms of said $(CH_2)_n$ and $(CH_2)_{n+1}$ may be bridged by a one or two carbon atom linkage, or any one pair of adjacent carbon atoms of said $(CH_2)_n$ and $(CH_2)_{n+1}$ may form, together with from one to three carbon atoms that are not members of the carbonyl containing ring, a ($C_3$–$C_5$) fused carbocyclic ring;

X is $(CH_2)_q$ wherein q is three and wherein one of the carbon-carbon single bonds in said $(CH_2)_q$ may optionally be replaced by a carbon-carbon double bond, and wherein any one of the carbon atoms of said $(CH_2)_q$ may optionally be substituted with $R^6$, and wherein any one of the carbon atoms of said $(CH_2)_q$ may optionally be substituted with $R^7$;

$R^6$ and $R^7$ are independently selected from hydrogen, hydroxy, halo, amino, oxo (=O), cyano, hydroxy-($C_1$–$C_6$)alkyl, ($C_1$–$C_6$)alkoxy-($C_1$–$C_6$)alkyl, ($C_1$–$C_6$) alkylamino, di-($C_1$–$C_6$)alkylamino,

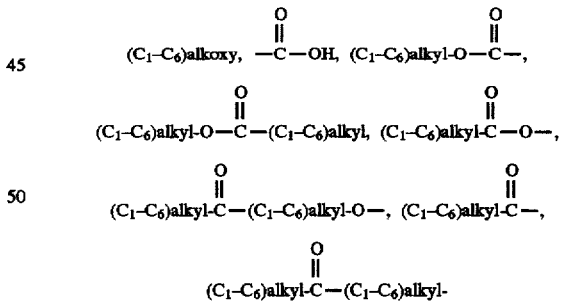

and the radicals set forth in the definition of $R^2$; and

Y is $(CH_2)_z$ wherein z is zero or one;

with the proviso that: (a) when A is —$(CH_2)$— or carbonyl, $R^5$ cannot be furyl, pyridyl, isothiazolyl, oxazolyl, triazolyl, tetrazolyl, quinolyl, thiazolyl or thienyl; (b) when m is zero, one of $R^3$ and $R^4$ is absent and the other is hydrogen; (c) when $R^6$ or $R^7$ is attached to a carbon atom of X that is adjacent to the ring nitrogen, then $R^6$ or $R^7$, respectively, must be a substituent wherein the point of attachment is a carbon atom; and (d) when Z is O or $CH_2$, z is one.

or a pharmaceutically acceptable salt of such compound.

2. A compound according to claim 1, wherein Z is NH.

3. A compound according to claim 1, wherein z is one.

4. A compound according to claim 1, wherein m is zero, $R^3$ is hydrogen and $R^4$ is absent.

5. A compound according to claim 1, wherein $R^6$ and $R^7$ are both hydrogen.

6. A compound according to claim 1, wherein $R^1$ is phenyl substituted with from one to three substituents independently selected from $(C_1-C_6)$alkyl optionally substituted with from one to three fluorine atoms and $(C_1-C_6)$alkoxy optionally substituted with from one to three fluorine atoms.

7. A compound according to claim 1, wherein z is one, m is zero, $R^4$ is absent and each of $R^3$, $R^6$ and $R^7$ is hydrogen.

8. A compound according to claim 7, wherein $R^1$ is phenyl substituted with from one to three substituents independently selected from $(C_1-C_6)$alkyl optionally substituted with from one to three fluorine atoms and $(C_1-C_6)$alkoxy optionally substituted with from one to three fluorine atoms.

9. A compound according to claim 1 that is selected from the group consisting of:

(±)-[3R-[3α,6α(R*)]]-3-phenyl-7-phenyl-1,8-diazaspiro[5.5]undecane;

(±)-[3R-[3α,6α(R*)]]-3-(2-methoxyphenyl)-7-phenyl-1,8-diazaspiro[5.5]undecane;

and the pharmaceutically acceptable salts of the foregoing compounds.

10. A compound according to claim 1, wherein z is one and q is three.

11. A compound according to claim 1, wherein z is one, q is three, m is zero, $R^3$ is hydrogen and $R^4$ is absent.

12. A compound according to claim 1, wherein z is one, q is three, m is zero, $R^3$ is hydrogen, $R^4$ is absent and $R^1$ is phenyl substituted with from one to three substituents independently selected from $(C_1-C_6)$alkyl optionally substituted with from one to three fluorine atoms and $(C_1-C_6)$alkoxy optionally substituted with from one to three fluorine atoms.

13. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

14. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

15. A compound of the formula

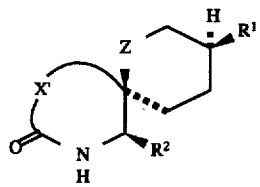

XVIII wherein Z, $R^1$ and $R^2$ are defined as in claim 1 and X' is $(CH_2)_2$.